United States Patent
Schmit et al.

(10) Patent No.: US 8,017,567 B2
(45) Date of Patent: *Sep. 13, 2011

(54) PERSONAL CLEANSING BAR WITH FREE FATTY ACID AND QUATERNARY SURFACTANT SYNERGISM

(75) Inventors: Catherine Schmit, Glendale, AZ (US); James Dalton, Scottsdale, AZ (US); Celeste Rosenberg, Scottsdale, AZ (US); E. Gary Myers, Scottsdale, AZ (US); Robert Dail, Phoenix, AZ (US)

(73) Assignee: The Dial Corporation, Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 11/465,581

(22) Filed: Aug. 18, 2006

(65) Prior Publication Data

US 2007/0042920 A1 Feb. 22, 2007

Related U.S. Application Data

(60) Provisional application No. 60/709,718, filed on Aug. 19, 2005.

(51) Int. Cl.
*C11D 17/00* (2006.01)

(52) U.S. Cl. ........ 510/153; 510/141; 510/133; 510/154; 510/155; 510/152; 510/130; 510/135; 510/123

(58) Field of Classification Search .......... 510/141, 510/152, 153, 154, 155, 130, 133, 135, 123, 510/240, 259

See application file for complete search history.

(56) References Cited

U.S. PATENT DOCUMENTS

| | | | | |
|---|---|---|---|---|
| 5,154,849 | A * | 10/1992 | Visscher et al. | 510/150 |
| 5,496,488 | A * | 3/1996 | Kacher et al. | 510/146 |
| 5,653,970 | A * | 8/1997 | Vermeer | 424/70.24 |
| 5,720,961 | A * | 2/1998 | Fowler et al. | 424/401 |
| 6,491,933 | B2 * | 12/2002 | Lorenzi et al. | 424/401 |
| 6,534,687 | B2 * | 3/2003 | Schultz et al. | 570/152 |
| 6,537,954 | B2 * | 3/2003 | Schultz et al. | 510/152 |
| 6,589,923 | B2 * | 7/2003 | Lenuck et al. | 510/155 |
| 6,616,922 | B2 * | 9/2003 | Taylor et al. | 424/70.28 |
| 6,846,787 | B1 * | 1/2005 | Farrell et al. | 510/152 |
| 6,949,493 | B1 * | 9/2005 | Zhang et al. | 510/141 |
| 2002/0016271 | A1 * | 2/2002 | Racherla | 510/141 |
| 2002/0039977 | A1 * | 4/2002 | Farrell et al. | 510/141 |
| 2002/0045555 | A1 * | 4/2002 | Andreas et al. | 510/141 |
| 2002/0098995 | A1 * | 7/2002 | Goo et al. | 510/141 |
| 2003/0104958 | A1 * | 6/2003 | Puvvada et al. | 510/141 |
| 2003/0134762 | A1 * | 7/2003 | Finucane et al. | 510/141 |
| 2005/0123574 | A1 * | 6/2005 | Abbas et al. | 424/401 |
| 2007/0042919 | A1 * | 2/2007 | Schmit et al. | 510/130 |
| 2008/0125340 | A1 * | 5/2008 | Dail | 510/130 |

\* cited by examiner

*Primary Examiner* — Mark Eashoo
*Assistant Examiner* — Jane L Stanley
(74) *Attorney, Agent, or Firm* — David K. Benson

(57) ABSTRACT

A personal care cleansing composition having enhanced perceptible skin benefits, for example, by selecting certain ratios of quaternary ammonium compounds and free fatty acids. Additionally, in accordance with various aspects of the present invention, the present inventors have discovered that the addition of talc in varying percentages increases qualities to the user such as freshness, smoothness, lather and creaminess. Additionally, aspects relating to fragrance retention, deposition and the amounts perceived are improved.

8 Claims, 1 Drawing Sheet

PERSONAL CLEANSING BAR WITH FREE FATTY ACID AND QUATERNARY SURFACTANT SYNERGISM

FIELD OF INVENTION

The present invention relates generally to personal care cleansing compositions having enhanced skin feel attributes, and more particularly to such compositions in solid form and even more particularly to soap bars exhibiting enhanced skin feel attributes, aesthetic qualities and processing capabilities.

BACKGROUND OF THE INVENTION

Personal care compositions such as toilet soaps are of course well known. Toilet soaps in bar form are usually formulated with a large variety of additives to provide benefits that are not inherent in the soap itself. For example, additives are employed to enhance the lathering of the soap, to enhance the mildness of the soap, to enhance its antibacterial effectiveness and numerous other benefits for the user. Additionally, various additives, such as talc, may be employed to reduce cost and provide various benefits to the user.

Commercial soap bars conventionally comprise one or more "soaps," which, for purposes of describing this component of the compositions of the present invention, have the meaning as normally understood in the art: monovalent salts of monocarboxylic fatty acids.

The counterions of the salts generally include sodium, potassium, ammonium and alkanol ammonium ions, but may include other suitable ions known in the art. The soap bars may also include optional adjuvant ingredients such as moisturizers, humectants, antibacterials, water, fillers, polymers, dyes, fragrances and the like, to effect cleansing and/or conditioning of the skin of the user.

Typically, the soap components in conventional soap bars comprise salts of long chain fatty acids having chain links of the alkyl group of the fatty acids from about 8 carbon atoms, to about 18 carbon atoms in length. The particular length of the alkyl chain of the soaps is selected for various reasons including cleansing capability, lather capability, cost, and the like.

Among the additives employed in the production of toilet soap bars are free fatty acids (FFA) which serve to enhance the lathering or foaming ability of the bars. Such fatty acids also have an affect on the mildness of the soap. Quaternary ammonium compounds (Quat) and other cationic cosmetic ingredients have been used in "wash-off" cleansing products such as liquid body washes for their enhanced deposition on skin due to the ionic attraction between the cationic quaternary ammonium compound and skin protein.

However, many cationic cosmetic materials are not compatible in soap, combars (mixtures of soap and synthetic detergents) and even syndet cleansing compositions due to the anionic materials in most of these matrices.

Accordingly, there is a need for cleansing compositions such as toilet soap bars that exhibit enhanced skin feel attributes.

SUMMARY OF THE INVENTION

The present inventors have discovered that there is surprising and unexpected synergy believed to be a result of interaction between certain Quats and FFAs, namely, enhanced perceptible skin benefits in personal cleansing soap bar compositions. It is believed that such benefits may also apply to a combar and/or a synthetic detergent composition containing soap in some proportion. The inventors have found that by selecting certain ratios of Quat and FFAs, and when such additives are employed in certain definitive proportions in personal care compositions, resulting data nearly uniformly supports the unexpected finding of enhanced perceptible skin benefits. As described herein, resulting data supports the same.

Additionally, in accordance with various aspects of the present invention, the present inventors have discovered that the addition of talc in varying percentages increases qualities to the user such as freshness, smoothness, lather and creaminess. Additionally, aspects relating to fragrance retention, deposition and the amounts perceived are improved.

BRIEF DESCRIPTION OF THE DRAWINGS

A more complete understanding of the present invention may be derived by referring to the detailed description and claims when considered in connection with the Figures, where like reference numbers refer to similar elements throughout the Figures, and wherein

DETAILED DESCRIPTION

Figure 1:
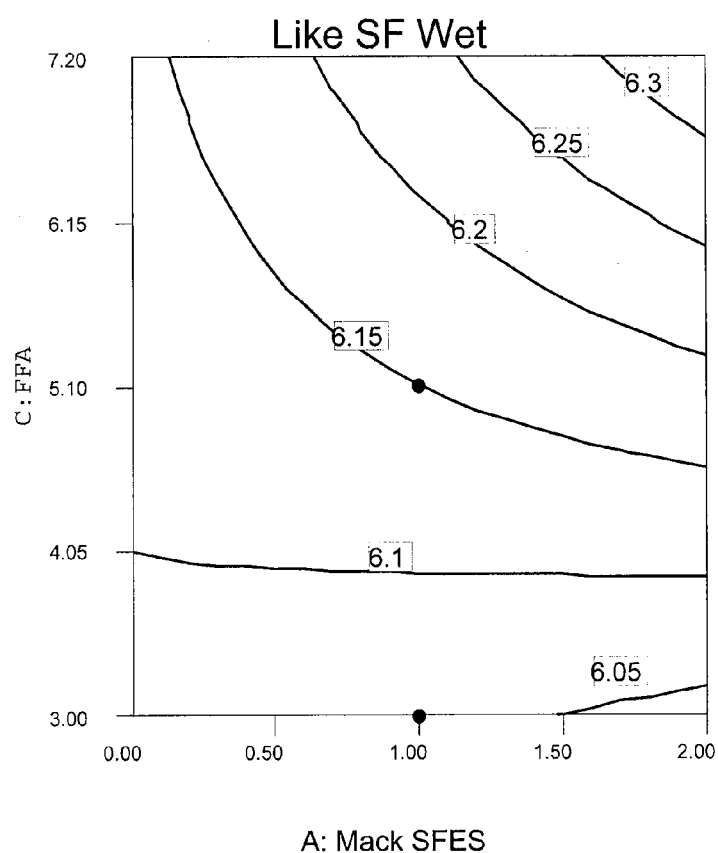
FIG. 1 is a response contour plot which visually shows the testing results.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

As noted above, the present inventors have discovered an unexpected synergistic result when employing certain levels of Quats and FFAs to give a superior skin feel to users of cleansing products employing such a combination. More specifically, surprisingly, users find an enhanced skin benefit of improved wet skin feel when bathing with personal care products (i.e., soap) having this combination. As used herein, "wet skin feel" means a positively perceived wet skin feel after washing or bathing with such compositions and thereafter rinsing the skin.

In accordance with various embodiments of the present invention as discussed below, this enhanced skin feel was perceived, near uniformily, when the level of Quats in the composition ranges from about 0.03% to about 1.5% by weight of the composition and the level of FFA ranges from about 4% to in excess of about 8%, most preferred from about 4.5% to about 7.5% of weight. The ratio of the FFA to the Quat should range from about 4:1 to about 195:1 with a preferred ratio of about 4:1 to about 19:1. The foregoing is based on 100% active components.

Quaternary Ammonium Compounds

The Quats useful in this invention are positively charged tetra substituting nitrogen derivatives of the following class:

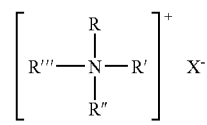

In which R, R', R" and R'", may be the same or different alkyl groups may not be hydrogen and in which X is a typical anion such as chloride or methosulfate. The particular Quat used in the following examples in the testing was Sunflowerseedamidopropyl Ethyldimonium Ethosulfate (INCI name) and available as Mackernium SFES from McIntyre Group. This commercial product contains about 70-75% of the active quaternary and about 25-30% by weight of PEG-9. The structure for this quaternary is [RC(O)—NH(CH$_2$)$_3$—N(CH$_3$)$_2$—CH$_2$—CH$_3$]$^+$CH$_3$—CH$_2$—OSO$_3$, or otherwise expressed as:

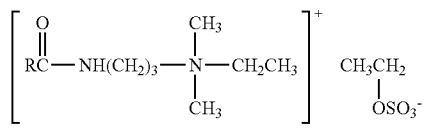

Alternative aliphatic groups may be substituted for those derived from sunflowerseed oil in this quaternary structure and the synergistic interaction with FFA is still expected to provide wet skin feel benefits. These aliphatic groups are of the structure RCO— where R is a C6 to C26 alkyl, alkenyl, alkadienyl, alkapolyenyl radical (straight or branched chain) or mixtures thereof.

Exemplary, additional Quats, that is a long chain alkylamidopropyl ethyldimonium ethosulfates having alkyl groups derived from various sources may be employed in this invention and include:

Apricotamidopropyl Ethyldimonium Ethosulfate
Behenamidopropyl Ethyldimonium Ethosulfate
Canolamidopropyl Ethyldimonium Ethosulfate.
C10-40 Isoalkylamidopropylethyldimonium Ethosulfate
C14-20 Isoalkylamidopropylethyldimonium Ethosulfate
C18-22 Isoalkylamidopropylethyldimonium Ethosulfate
Cocamidopropyl Ethyldimonium Ethosulfate
Isononamidopropyl Ethyldimonium Ethosulfate
Isostearamidopropyl Ethyldimonium Ethosulfate
Lanolinamidopropyl Ethyldimonium Ethosulfate
Linoleamidopropyl Ethyldimonium Ethosulfate
Methyleicosamidopropyl Ethyldimonium Ethosulfate
Minkamidopropyl Ethyldimonium Ethosulfate
Oleamidopropyl Ethyldimonium Ethosulfate
Rapeseedamidopropyl Ethyldimonium Ethosulfate
Ricinoleamidopropyl Ethyldimonium Ethosulfate
Saffloweramidopropyl Ethyldimonium Ethosulfate
Soyamidopropyl Ethyldimonium Ethosulfate
Stearamidopropyl Ethyldimonium Ethosulfate
Wheatgermamidopropyl Ethyldimonium Ethosulfate That said, the foregoing exemplary compositions are non-limiting, and those skilled in the art may find alternative examples, and still fall within the scope of the present invention.

The following oils may also be a source of the fatty acids for "RCO—" in the above formula:

Black currant seed oil
Borage seed oil
Corn oil
Evening primrose oil
Grapeseed oil
Kukui nut oil
Peanut oil Again, the foregoing exemplary compositions are non-limiting, and those skilled in the art may find alternative examples, and still fall within the scope of the present invention.

Fatty Acid Components

The FFA employed in the examples is palm acid which is a mixture of fatty acids derived from palm oil. It is commercially available from The Dial Corporation as "Palm Stearin Fatty Acid." Other exemplary useful fatty acids include, but are not limited to:

Arachidic Acid
Arachidonic Acid
Beeswax Acid
Behenic Acid
Capric Acid
Caproic Acid
Caprylic Acid
C10-40 Hydroxyalkyl Acid
C10-40 Isoalkyl Acid
C32-36 Isoalkyl Acid
Coconut Acid
Corn Acid
Cottonseed Acid
Erucic Acid
Hydrogenated Coconut Acid
Hydrogenated Menhaden Acid
Hydrogenated Palm Acid
Hydrogenated Tallow Acid
Hydroxystearic Acid
Isomerized Linoleic Acid
Isomerized Safflower Acid
Isostearic Acid
Lauric Acid
Linoleic Acid
Linolenic Acid
Linseed Acid
Myristic Acid
Oleic Acid
Olive Acid
Palmitic Acid
Palm Kernel Acid
Peanut Acid
Pelargonic Acid
Rapeseed Acid
Rice Bran Acid
Ricinoleic Acid
Safflower Acid
Soy Acid
Stearic Acid
Sunflower Seed Acid
Tall Oil Acid
Tallow Acid
Undecanoic Acid
Undecylenic Acid
Wheat Germ Acid And again, the foregoing exemplary compositions are non-limiting, and those skilled in the art may find alternative examples, and still fall within the scope of the present invention.

As noted above, when maintaining the ratios of Quats to FFAs described herein, surprisingly, an enhanced skin benefit was found. It is believed that is, at least in part, the maintenance of these ratios which results in a synergy, providing such benefits.

In support, to predict various soap bar formulas with consumer preference sensory benefits a Design of Experiment (DOE) approach was used. One of the key desired sensory attributes was, "liking of wet skin feel during bar use." The test involved eleven soap bar products as shown in the following chart:

| | DOE Personal Cleansing Bar Formulas | | | | | |
|---|---|---|---|---|---|---|
| | 1 | 2 | 3 | 4 | 5 | 6 |
| | | | | Bar: | | |
| Component | Control Weight % | Prototype 1 Weight % | 2% Mackernium SFES Weight % | 4% PEG-12 Weight % | 7.2% FFA pellet Weight % | 2% Mackernium 4% PEG-12 Weight % |
| Sodium Soap | 81.39 | 80.40 | 79.40 | 77.65 | 78.22 | 75.65 |
| Palm Stearin Free Fatty Acid | 2.82 | 2.82 | 2.82 | 2.82 | 6.00 | 2.82 |
| Water | 11.63 | 11.63 | 11.63 | 11.63 | 11.63 | 11.63 |
| Perfume | 1.50 | 1.50 | 1.50 | 1.50 | 1.50 | 1.50 |
| Titanium Dioxide | 0.40 | 0.40 | 0.40 | 0.40 | 0.40 | 0.40 |
| Glycerin | | | | Less than 1% | | |
| Sorbitol | | | | 1-2% | | |
| Sodium Chloride | | | | Less Than 1% | | |
| Aloe barbadensis leaf juice | | | | Less Than 1% | | |
| Pentasodium Pentetate | | | | Less Than 1% | | |
| Tetrasodium Etidronate | | | | Less Than 1% | | |
| Chromium hydroxide green | | | | Less Than 1% | | |
| Yellow 5 | | | | Less Than 1% | | |
| New Ingredients May Include: | | | | | | |
| Mackernium SFES | 0.00 | 1.00 | 2.00 | 0.00 | 0.00 | 2.00 |
| PEG-12 | 0.00 | 0.00 | 0.00 | 4.00 | 0.00 | 4.00 |
| Total: | 100.00 | 100.00 | 100.00 | 100.00 | 100.00 | 100.00 |

| | 7 | 8 | 9 | 10 | 11 |
|---|---|---|---|---|---|
| | | | Bar: | | |
| Component | 2% Mackernium 7.2% FFA pellet Weight % | 4% PEG-12 7.2% FFA pellet Weight % | 2% Mackernium 4% PEG-12 7.2% FFA Pellets Weight % | 1% Mackernium 2% PEG-12 5.1% FFA Pellets Weight % | 1% Mackernium 2% PEG-12 Weight % |
| Sodium Soap | 76.22 | 74.47 | 72.47 | 77.07 | 78.65 |
| Palm StearIn Free Fatty Acid | 6.00 | 6.00 | 6.00 | 4.40 | 2.82 |
| Water | 11.63 | 11.63 | 11.63 | 11.63 | 11.63 |
| Perfume | 1.50 | 1.50 | 1.50 | 1.50 | 1.50 |
| Titanium Dioxide | 0.40 | 0.40 | 0.40 | 0.40 | 0.40 |
| Glycerin | | | Less Than 1% | | |
| Sorbitol | | | 1-2% | | |
| Sodium Chloride | | | Less Than 1% | | |
| Aloe barbadensis leaf juice | | | Less Than 1% | | |
| Pentasodium Pentetate | | | Less Than 1% | | |
| Tetrasodium Etidronate | | | Less Than 1% | | |
| Chromium hydroxide green | | | Less Than 1% | | |
| Yellow 5 | | | Less Than 1% | | |
| New Ingredients May Include: | | | | | |
| Mackernium SFES | 2.00 | 0.00 | 2.00 | 1.00 | 1.00 |
| PEG-12 | 0.00 | 4.00 | 4.00 | 2.00 | 2.00 |
| Total: | 100.00 | 100.00 | 100.00 | 100.00 | 100.00 |

The panelists were females ages 18-54 with a total of 200 panelists for each of the 11 bar products. Each panelist used 6 of the 11 bar soaps during a sequential monadic one week use period. The panelists were asked various questions about their perception of the sensory benefits. A key question was, "overall how much did you like or dislike the way your wet skin felt after washing and rinsing?" Responses were on a 1-9 point scale with 1 being "disliked extremely" and 9 being "liked extremely."

The resulting data supports a conclusion that cleansing products in accordance with the present invention result, surprisingly and nearly uniformly, in exhibiting the enhanced skin benefit of wet skin feel. In this regard, it would appear that a synergistic effect results when the ranges of Quats and FFAs are maintained as disclosed herein, perhaps because of interaction between FFA and Quats. This is best seen on a response contour plot of the consumer test data. Increasing the level of Quat had a larger affect on wet skin feel liking as the FFA level increased. PEG-12 did not show a significant affect on "liking wet skin feel."

FIG. 1 illustrates the response contour plot that visually shows the effect of SFES and FFA levels on consumer's "liking wet skin feel" score. This plot represents the mathematically predicted score for all possible combinations of Mackernium SFES and FFA based on the actual data from the 11 bars tested in the DOE. Horizontal line A (x axis) shows the percent of Mackernium SFES used in the various bars and vertical line C (y axis) shows the percent of the free fatty acid used in the bars. Each contour line represents a different score for "like wet skin feel". Any combination of SFES and FFA along each line should provide a wet skin benefit with that liking score. In general, the score goes up as you increase FFA and SFES. However, the plot shows that the use of SFES at low levels of FFA provided little benefit to improving the liking wet skin feel score. More than about 4% by weight of the fatty acid was required to get a significant increase in wet skin feel benefit in combination with the SFES quaternary. This graph also shows that a significant positive benefit was found at a level of about 5% by weight of the free fatty acid in combination with the SFES quaternary.

The mathematical model for "liking wet skin feel" score derived from the test data was statistically significant (p-value=0.015). The full model equation is as follows:

$$\text{Like } SF \text{ Wet} = 6.053 - (0.115 \times \% \, SFES) + (0.012 \times \% \, FFA) + (0.030 \times .\% \, SFES \times .\% \, FFA)$$

This equation indicated that SFES and FFA each had individual affects on "liking wet skin feel," and SFES and FFA in combination also had a synergistic affect. The score for "like wet skin feel" can be predicted using this equation for any combination of SFES and FFA. Scoring is on a 1-9 scale with 1 being "disliked extremely" and 9 being "liked extremely." The 6.053 number indicated the baseline score for wet skin feel with the minimum amount of the ingredient variables tested; 0% SFES and 3% FFA. The "+" sign or "−" sign in front of each constant in the equation indicates, if that ingredient (or combination of ingredients) increases, the "liking wet skin feel" score either increases or decreases (respectively) by that constant times the % of those ingredients in the cleansing formula. As can be seen by the "−" sign in front of the SFES factor, SFES used alone has a negative affect on "like wet skin feel." But as can be seen by the "+" sign in front of the (SFES×FFA) factor, SFES interacting with FFA has a positive synergistic affect on "liking wet skin feel." FFA also individually has a positive affect on "liking wet skin feel." In order to increase the "liking wet skin feel" score above the baseline score of 6.053, the levels of SFES and FFA need to have a net positive affect on the score.

In addition to Mackernium SFES, other similar quaternaries, as listed previously, would also be expected to have a synergistic positive benefit when used with FFA. The levels that have the net positive benefit can be predicted from the mathematical model equation. Such levels are:

Total level (proportion) of Quat is about 0.03% to about 1.50%, with a preferred range of about 0.35% to about 1.1 % (based on a 100% active quat).

Total level of FFAs is about 4% to about 8% by weight with a preferred range of about 4.5% to about 7.5%.

The ratio of the FFA to the Quat is from about 4:1 to about 195:1 with a preferred ratio of about 4:1 to about 19:1.

Talc Components

As noted above, the addition of talc to cleansing bars in accordance with various embodiments of the present invention, results in user perceived benefits such as freshness, smoothness, lather generation and creaminess. Additionally, aspects relating to fragrance retention, deposition and the amounts perceived are improved. Further still the addition of talc may result in substantial costs savings. For example, the level of talc in cleansing bars such as those described above ranges from about 5% to about 10% by weight of the composition, and preferably about 7% by weight of the composition.

In accordance with various aspects of the present invention, improved processing techniques for the addition of talc are provided for herein. For example, beginning with a personal cleansing bar in comprises about 1% by weight of 1% Mackemium SFES (Sunflowerseedamidopropyl Ethylidimonium Ethosulfate), about 2% PEG 12, and soap pellets with about 2.8% by weight FFA and 1.5% by weight fragrance.

In running bars of the forgoing formula, as shown in below, it was found that processing speeds on the soap finishing line fell approximately 20% when compared to a control bar (a no additive soap formula with only color and fragrance). It was found that the addition of talc (e.g., Magnesium Silicate), greatly improved the soap finishing line efficiency as measured in extruded bar slugs per minute when either about 10% or about 15% talc was added to the amalgamator (see e.g., FIGS. 2 and 3) to the forgoing formula.

Benefits of such processing techniques result in soap bars that tend not to crack or slough, i.e., get soft or mushy in the presence of water. Additionally, as noted above, surprisingly, high levels of talc in the soap bars additionally offer improved amounts of small bubble, creamy lather. The increase in lather is a novel finding since one would normally expect less lather as the soap is replaced by a generally inert filler. Test data confirms the same; hand wash panels and tests in agitated, graduated cylinders demonstrate the product improvement in amount of small bubble, creamy lather and the quantity of lather. Additionally, the use of talc to replace soap, results in significant cost savings. For example, stearilized talc or antibacterial bars costing $0.18/lb. and non-stearilized costing 0.10/lb. versus soap at $0.32/lb., the cost savings are significant, particularly in the context of large scale manufacturing.

Exemplary Compositions

The following tables illustrate exemplary compositions in accordance with the present invention.

EXAMPLE 1

| Component/INCI Name | Function | Weight, % |
| --- | --- | --- |
| Soap (sodium cocoate, sodium palm kernalate, sodium palmate, sodium tallowate | Cleansing, lather, foam | 70.64285 |
| Water (Aqua) | Processing aid | 11.96353 |
| Talc | Filler/Skin Feel | 5.02636 |
| Coconut Acid, Palm Acid, Tallow Acid | Lather enhancer, emollient | 4.56369 |
| PEG-6 Methyl Ether | Solvent/Processing aid | 4.01810 |
| Perfume (Parfum) | Perfume, smell | 1.10200 |
| Glycerin | Moisturizer, processing aid | 0.00005 |
| Sorbitol | Moisturizer, processing aid | 0.92194 |
| Triclocarban | Antibacterial agent | 0.77963 |
| Sodium Chloride | Processing aid | 0.77295 |
| Pentasodium Pentetate | Chelating agent | 0.09692 |
| Tetrasodium Etidronate | Chelating agent | 0.09583 |
| Yellow No. 5 (CI 19140) | Colorant | 0.01332 |
| Yellow No. 8 (CI45350) | Colorant | 0.00212 |
| Red No. 4 (CI 14700) | Colorant | 0.00071 |

EXAMPLE 2

| Component/INCI Name | Function | Weight, % |
| --- | --- | --- |
| Soap (sodium cocoate, sodium palm kernalate, sodium palmate, sodium tallowate | Cleansing, lather, foam | 71.33758 |
| Water (Aqua) | Processing aid | 12.20687 |
| Talc | Filler/Skin Feel | 5.07580 |
| Coconut Acid, Palm Acid, Tallow Acid | Lather enhancer, emollient | 4.60857 |
| PEG-12 | Humectant/Moisturizer | 2.15023 |
| Theobroma Cacao (Cocoa) Seed Butter | Skin care additive | 1.27507 |
| Fragrance (Parfum) | Perfume, smell | 1.16293 |

-continued

| Component/INCI Name | Function | Weight, % |
|---|---|---|
| Glycerin | Moisturizer, processing aid | 0.00003 |
| Sorbitol | Moisturizer, processing aid | 0.93099 |
| Sodium Chloride | Processing aid | 0.78055 |
| Decyl Glucoside | Lather booster | 0.10001 |
| Extract Blend | Skin care additive | 0.10001 |
| Pentasodium Pentetate | Chelating agent | 0.09788 |
| Tetrasodium Etidronate | Chelating agent | 0.09677 |
| Titanium Dioxide (CI 77891) | Brightener/Colorant | 0.07001 |
| Iron Oxide (CI 77491) & Talc (CI 77718) | Colorant | 0.00670 |

EXAMPLE 3

| Component/INCI Name | Function | Weight, % |
|---|---|---|
| Soap (sodium cocoate, sodium palm kernalate, sodium palmate, sodium tallowate | Cleansing, lather, foam | 72.36887 |
| Water (Aqua) | Processing aid | 13.06276 |
| Talc | Filler/Skin Feel | 5.14918 |
| Coconut Acid, Palm Acid, Tallow Acid | Lather enhancer, emollient | 4.67520 |
| Fragrance (Parfum) | Perfume, smell | 1.41004 |
| Glycerin | Moisturizer, processing aid | 0.89683 |
| Sorbitol | Moisturizer, processing aid | 0.94444 |
| Sodium Chloride | Processing aid | 0.79183 |
| Titanium Dioxide (CI 77891) | Brightener/Colorant | 0.29997 |
| Pentasodium Pentetate | Chelating agent | 0.09929 |
| Tetrasodium Etidronate | Chelating agent | 0.09817 |
| Ultramarines (CI 77007) | Colorant | 0.15136 |
| Chromium Hydroxide Green (CI 77289) | Colorant | 0.05206 |

Last, in the foregoing specification, the invention has been described with reference to specific embodiments. However, one of ordinary skill in the art appreciates that various modifications and changes can be made without departing from the scope of the present invention as set forth in the claims below. Accordingly, the specification is to be regarded in an illustrative rather than a restrictive sense, and all such modifications are intended to be included within the scope of the present invention.

Benefits, other advantages, and solutions to the problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A bar soap composition comprising:
    at least one alkylamidopropyl ethyldimonium ethosulfate compound in an amount of from about 0.1% to about 1.5% by weight of the bar soap composition and selected from the group consisting of canolamidopropyl ethyldimonium ethosulfate, linoleamidopropyl ethyldimonium ethosulfate, oleamidopropyl ethyldimonium ethosulfate, ricinoleamidopropyl ethyldimonium ethosulfate, saffloweramidopropylethyldimonium ethosulfate, sunflowerseedamidopropyl ethyldimonium ethosulfate, and soyamidopropyl ethyldimonium ethosulfate;
    a free fatty acid in an amount of about 4.7% to about 7.2% by weight of the bar soap composition and selected from the group consisting of palm stearin, linoleic acid, myristic acid, oleic acid, palmitic acid, and stearic acid, and mixtures thereof, said free fatty acid in a ratio with said alkylamidopropyl ethyldimonium ethosulfate in a range from about 4:1 to about 19:1 and
    talc in an amount of from about 5% to 10% by weight of the personal cleansing composition.

2. The bar soap composition according to claim 1, wherein said talc is about 5% by weight of the bar soap composition.

3. The bar soap composition according to claim 1 further comprising PEG-9, wherein a ratio of said alkylamidopropyl ethyldimonium ethosulfate to said PEG-9 ranges from about 7:3 to about 3:1.

4. The bar soap composition according to claim 1 further comprising PEG-12 in an amount of less than about 4% by weight of the bar soap composition.

5. A bar soap composition comprising:
    at least one alkylamidopropyl ethyldimonium ethosulfate compound in an amount of from about 0.1% to about 1.5% by weight of the bar soap composition and selected from the group consisting of canolamidopropyl ethyldimonium ethosulfate, linoleamidopropyl ethyldimonium ethosulfate, oleamidopropyl ethyldimonium ethosulfate, ricinoleamidopropyl ethyldimonium ethosulfate, saffloweramidopropylethyldimonium ethosulfate, sunflowerseedamidopropyl ethyldimonium ethosulfate, and soyamidopropyl ethyldimonium ethosulfate; and
    a free fatty acid in an amount of about 4.7% to about 7.2% by weight of the bar soap composition and selected from the group consisting of palm stearin, linoleic acid, myristic acid, oleic acid, palmitic acid, and stearic acid, and mixtures thereof, said free fatty acid in a ratio with said alkylamidopropyl ethyldimonium ethosulfate in a range from about 4:1 to about 19:1.

6. The bar soap composition according to claim 5, further comprising PEG-9, wherein a ratio of said alkylamidopropyl ethyldimonium ethosulfate to said PEG-9 ranges from about 7:3 to about 3:1.

7. The bar soap composition according to claim 5, further comprising PEG-12 in an amount of less than about 4% by weight of the bar soap composition.

8. The bar soap composition according to claim 5, wherein the at least one alkylamidopropyl ethyldimonium ethosulfate comprises sunflowerseedamidopropyl ethyldimonium ethosulfate.

* * * * *